(12) United States Patent
Ruat et al.

(10) Patent No.: US 9,061,997 B2
(45) Date of Patent: Jun. 23, 2015

(54) QUINOLINONE DERIVATIVES

(75) Inventors: Martial Ruat, Orsay (FR); Hélène Faure, Gif-sur-Yvette (FR); Tatiana Gorojankina, Gif-sur-Yvette (FR); André Mann, Ostwald (FR); Maurizio Taddei, Monteriggioni (IT); Fabrizio Manetti, Castelnuevo Berardenga (IT); Antonio Solinas, Siena (IT)

(73) Assignee: Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 13/885,089

(22) PCT Filed: Nov. 15, 2011

(86) PCT No.: PCT/IB2011/055096
§ 371 (c)(1),
(2), (4) Date: Jun. 12, 2013

(87) PCT Pub. No.: WO2012/066478
PCT Pub. Date: May 24, 2012

(65) Prior Publication Data
US 2013/0267559 A1 Oct. 10, 2013

(30) Foreign Application Priority Data
Nov. 16, 2010 (FR) ..................... 10 04445

(51) Int. Cl.
*C07D 215/22* (2006.01)
*A61K 31/4704* (2006.01)
*C07D 215/56* (2006.01)

(52) U.S. Cl.
CPC .......... *C07D 215/22* (2013.01); *A61K 31/4704* (2013.01); *C07D 215/56* (2013.01)

(58) Field of Classification Search
CPC ............. A61K 31/4704; A01B 12/006; C07D 215/22; C07D 215/56
USPC ........................... 546/159, 163; 514/312, 338
See application file for complete search history.

(56) References Cited

U.S. PATENT DOCUMENTS

| | | | | |
|---|---|---|---|---|
| 4,547,511 A | * | 10/1985 | Eriksoo et al. | 514/312 |
| 4,738,971 A | * | 4/1988 | Eriksoo et al. | 514/312 |
| 4,738,974 A | * | 4/1988 | Brandstrom | 514/338 |
| 8,183,236 B2 | * | 5/2012 | Neamati et al. | 514/217.07 |

FOREIGN PATENT DOCUMENTS

| WO | WO-00/01386 | | 1/2000 |
|---|---|---|---|
| WO | 2008/014307 | * | 1/2008 |
| WO | 20085/014307 | * | 1/2008 |

OTHER PUBLICATIONS

Ukrainets, Chem of Het Comp, vol. 43, No. 12, 2007, p. 1532-1539.*
Ukrainets, Chem of Het Comp, vol. 43, vol 1, 2007, p. 63-66.*
Ukrainets,CA 120:270304, abstract only of Khimiya Geterotsiklicheskikh Soedinenii, vol. 9, 1993, pp. 1223-1226.*
Ukrainets, Chem of Het Comp, vol. 43, no. 12, 2007, pp1532-1539.*
Ukrainets, Chem of Het Comp, vol. 43, no. 1, 2007, pp. 63-66.*
Ukrainets, CA 120:270304, abstract only of Khimiya Geterotsiklicheskikh Soedinenii, vol. 9, 1993, pp. 1223-1226.*
Aghaloo, T. L., et al.; "*Oxysterols enhance osteoblast differentiation in vitro and bone healing in vivo*;" J Orthop Res, vol. 25, No. 11; pp. 1488 97; dated Jun. 2007; abstract retrieved on Jun. 18, 2013 from <http://onlinelibrary.wiley.com/doi/10.1002/jor.20437/abstract;jsessionid=AF58A5251B2E543DB70E4FB96E4E4026.d01t02>.
Amantea, C. M., et al.; "*Oxysterol-induced osteogenic differentiation of marrow stromal cells is regulated by Dkk-1 inhibitable and PI3-kinase mediated signaling*;" J Cell Biochem, vol. 105, No. 2; pp. 424-436; dated Oct. 2008; retrieved on Jun. 18, 2013 from <http://www.ncbi.nlm.nih.gov/pmc/articles/PMC2574814/pdf/nihms-65799.pdf>.
Beloti, M. M., et al., "*Purmorphamine enhances osteogenic activity of human osteoblasts derived from bone marrow mesenchymal cells*;" Cell Biol Int, vol. 29, No. 7; pp. 537-541; dated 2005; retrieved on Jun. 18, 2013 from <http://www-13.all-portland.net/cbi/029/0537/0290537.pdf>.
Boonen, S., et al.;"*Musculoskeletal effects of the recombinant human IGF-I/IGF binding protein-3 complex in osteoporotic patients with proximal femoral fracture: a double-blind, placebo-controlled pilot study*;" J Clin Endocrinol Metab, vol. 87, No. 4; pp. 1593-1599; dated 2002; retrieved on Jun. 18, 2013 from <http://jcem.endojournals.org/content/87/4/1593.full.pdf+html>.
Centrella, M., et al.; "*Transforming growth factor-beta gene family members and bone*;" Endocr Rev, vol. 15, No. 1; pp. 27-39; dated Feb. 1994; abstract retrieved on Jun. 18, 2013 from <http://edrv.endojournals.org/content/15/1/27.abstract>.
Chen, J. K., et al.; "*Small molecule modulation of Smoothened activity*;" Proc Natl Acad Sci USA, vol. 99, No. 22; pp. 14071-14076; dated 2002.

(Continued)

*Primary Examiner* — D M Seaman
(74) *Attorney, Agent, or Firm* — Alston & Bird LLP (57) ABSTRACT

The present invention relates to compounds which are quinolinone derivatives of general formula (I) capable of modulating the activity, in particular of inducing the differentiation, of stem and progenitor cells; these compounds are of use in the treatment of disorders related to a stem differentiation defect; the invention also relates to novel compounds among these quinolinone derivatives and to pharmaceutical compositions containing the same.

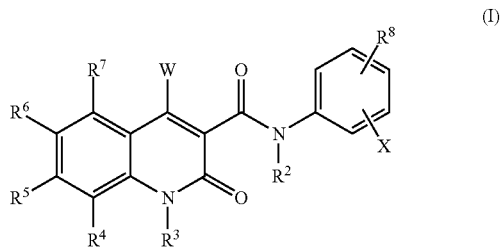

9 Claims, 5 Drawing Sheets (56) References Cited

OTHER PUBLICATIONS

Corcoran, R. B., et al.; "*Oxysterols stimulate Sonic hedgehog signal transduction and proliferation of medulloblastoma cells*;" Proc Natl Acad Sci USA, vol. 103, No. 22; pp. 8408-8413; dated May 2006; retrieved on Jun. 18, 2013 <http://www.ncbi.nlm.nih.gov/pmc/articles/PMC1462959/pdf/zpq8408.pdf>.

Dayam, et al.; "*Discovery and structure-activity relationship studies of a unique class of HIV-1 integrase inhibitors*;" Chem Med Chem, vol. 1, No. 20; pp. 238-244; dated Dec. 2005; abstract retrieved on Jun. 18, 2013 from <http://onlinelibrary.wiley.com/doi/10.1002/cmdc.200500018/abstract>.

Dwyer, J. R., et al.; "*Oxysterols are novel activators of the hedgehog signaling pathway in pluripotent mesenchymal cells*;" J Biol Chem, vol. 282, No. 12; pp. 8959-8968; dated Mar. 2007; retrieved on Jun. 18, 2013 from <http://www.jbc.org/content/282/12/8959.full.pdf+html>.

Frank-Kamenetsky, M., et al.; "*Small-molecule modulators of Hedgehog signaling: identification and characterization of Smoothened agonists and antagonists*;" J Biol, vol. 1, No. 2; pp. 10-10.19; dated Nov. 2002; retrieved on Jun. 18, 2013 from <http://www.ncbi.nlm.nih.gov/pmc/articles/PMC137065/pdf/1475-4924-1-10.pdf>.

Fromigue, O., et al.; "*Growth factors and bone formation in osteoporosis: roles for fibroblast growth factor and transforming growth factor beta*;" Curr Pharm Des, vol. 10, No. 21; pp. 2593-2603; dated 2004; abstract retrieved on Jun. 18, 2013 from <http://www.eurekaselect.com/62778/article>.

Giustina, A., et al.; "*Growth hormone, insulin-like growth factors, and the skeleton*;" Endocr Rev, vol. 29, No. 5; pp. 535-559; dated Aug. 2008; retrieved on Jun. 18, 2013 from <http://edrv.endojournals.org/content/29/5/535.full.pdf+html>.

Guan, C. C., et al.; "Sonic hedgehog alleviates the inhibitory effects of high glucose on the osteoblastic differentiation of bone marrow stromal cells"; Bone, vol. 45, No. 6; pp. 1146-1152; dated Dec. 2009; abstract retrieved on Jun. 18, 2013 from <http://www.thebonejournal.com/article/S8756-3282(09)01823-7/abstract>.

He, L., et al.; "*Probabilistic Neural Network Multiple Classifier System for Predicting the Genotoxicity of Quinolone and Quinoline Derivatives*;" Chem Res Toxicol, vol. 18; pp. 428-440; dated Aug. 2005.

Hu, H., et al.; "*Sequential roles of Hedgehog and Wnt signaling in osteoblast development*;" Development, vol. 132, No. 1; pp. 49-60; dated 2005.

Ingham, P. W., et al.; "*Hedgehog signaling in animal development: paradigms and principles*;" Genes Dev, vol. 15, No. 23; pp. 3059-3087; dated 2001; retrieved on Jun. 18, 2013 from <http://genesdev.cshlp.org/content/15/23/3059.full.pdf+html>.

Johnson, E. E., et al.; "*Human bone morphogenetic protein allografting for reconstruction of femoral nonunion*," Clin Orthop Relat Res, vol. 371; pp. 61-74; dated Feb. 2000; abstract retrieved on Jun. 18, 2013 <http://journals.lww.com/corr/Abstract/2000/02000/Human_Bone_Morphogenetic_Protein_Allografting_for.8.aspx>.

Lum, L. et al.; "*The Hedgehog response network: sensors, switches, and routers*;" Science, vol. 304, No. 5678; pp. 1755-1759; dated Jun. 2004; abstract retrieved on Jun. 18, 2013 from <http://www.sciencemag.org/content/304/5678/1755.abstract>.

Marti, E., et al.; "*Sonic hedgehog in CNS development: one signal, multiple outputs*;" Trends Neurosci, vol. 25, No. 2; pp. 89-96; dated Feb. 2002; abstract retrieved on Jun. 18, 2013 <http://www.cell.com/trends/neurosciences/abstract/S0166-2236(02)02062-3>.

Mohammad, K. S., et al.; "*Pharmacologic inhibition of the TGF-beta type I receptor kinase has anabolic and anti-catabolic effects on bone*;" PLoS One, vol. 4, No. 4; p. e5275; dated Apr. 2009; retrieved on Jun. 18, 2013 from <http://www.ncbi.nlm.nih.gov/pmc/articles/PMC2666804/pdf/pone.0005275.pdf>.

Pepinsky, R. B., et al.; "*Identification of a palmitic acid-modified form of human Sonic hedgehog*;" J Biol Chem, vol. 273, No. 22; pp. 14037-14045; dated May 1998; retrieved from <http://www.jbc.org/content/273/22/14037.full.pdf+html>.

Spinella-Jaegle, S., et al.; "*Sonic hedgehog increases the commitment of pluripotent mesenchymal cells into the osteoblastic lineage and abolishes adipocytic differentiation*;" J Cell Sci, vol. 114, Pt 11; pp. 2085-2094; dated Jun. 2001; retrieved on Jun. 18, 2013 from <http://jcs.biologists.org/content/114/11/2085.full.pdf+html>.

Ukrainets, I.V., et al.; "*4-hydroy-2-quinolones 138*;" Chemistry of Heterocyclic Compounds, vol. 43, No. 12; pp. 1532-1539; dated Dec. 2007.

Van der Horst, G., et al.; "*Hedgehog stimulates only osteoblastic differentiation of undifferentiated KS483 cells*;" Bone, vol. 33, No. 6; pp. 899-910; dated Dec. 2003; abstract retrieved on Jun. 18, 2013 from <http://www.thebonejournal.com/article/S8756-3282(03)00268-0/abstract>.

Varjosalo, M., et al.; "*Hedgehog: functions and mechanisms*;" Genes Dev, vol. 22, No. 18; pp. 2454-2472; dated 2008; retrieved on Jun. 18, 2013 <http://genesdev.cshlp.org/content/22/18/2454.full.pdf+html>.

Wechsler-Reya, R., et al.; "*The developmental biology of brain tumors*;" Annu Rev Neurosci, vol. 24; pp. 385-428; dated Jan. 2001; retrieved on Jun. 18, 2013 from <http://med.stanford.edu/labs/matthew_scott/pubs/Wechsler-Reya=AnaRevNS.pdf>.

Wu, X., et al.; "*Purmorphamine induces osteogenesis by activation of the hedgehog signaling pathway*;" Chem Biol, vol. 11, No. 9; pp. 1229-1238; dated Sep. 2004; retrieved on Jun. 18, 2013 from <http://download.cell.com/chemistry-biology/pdf/PIIS1074552104002212.pdf>.

Yamaguchi, A., et al.; "*Regulation of osteoblast differentiation mediated by bone morphogenetic proteins, hedgehogs, and Cbfa1*;" Endocr Rev, vol. 21, No. 4; pp. 393-411; dated Aug. 2000; retrieved on Jun. 18, 2013 from <http://edrv.endojournals.org/content/21/4/393.full.pdf+html>.

Yu, P. B., et al.; "*Dorsomorphin inhibits BMP signals required for embryogenesis and iron metabolism*;" Nat Chem Biol, vol. 4 No. 1; pp. 33-41 dated Jan. 2008 from <http://www.ncbi.nlm.nih.gov/pmc/articles/PMC2727650/pdf/nihms44146.pdf>.

International Search Report and Written Opinion for Application No. PCT/IB2011/055096; dated Feb. 23, 2012.

\* cited by examiner

QUINOLINONE DERIVATIVES

FIELD

The present invention relates to compounds which are quinolinone derivatives capable of modulating the activity, in particular of inducing the differentiation, of stem and progenitor cells; these compounds are of use in the treatment of disorders related to a cell differentiation defect; the invention also relates to novel compounds among these quinolinone derivatives and to pharmaceutical compositions containing same.

BACKGROUND

The repair of damaged tissues subsequent to a disease, a trauma or age increasingly uses stem or progenitor cells which retain the ability to differentiate into various cell types. These cells constitute a reservoir capable of renewing tissues in order to restore biological functions. Mesenchymal stem cells, for example, can give osteoblasts, chondrocytes, adipocytes, or stromal cells which are a support for hematoporesis.

The techniques which make it possible to direct these cells toward a chosen phenotype are generally laborious (transformation of cells using expression vectors and the need to express several genes) and alternative solutions such as the use of small synthetic differentiation-inducing molecules would constitute a promising approach.

Among the disorders resulting from a cell differentiation defect are those linked to a dysfunction of osteoblast differentiation.

Bone is continually renewed during life by means of a complex process involving resorption by osteoclasts and formation by osteoblasts.

Osteoblast precursors are pluripotent cells also known as mesenchymal stem cells. However, the mechanisms which allow these cells to differentiate into the osteoblast lineage are complex and are of great importance in the understanding of bone development. In addition, the identification of molecules which would induce osteoblast differentiation and would stimulate their osteogenic activity would represent a therapeutic approach in the treatment of bone diseases.

Indeed, many diseases are caused by dysregulation of osteoblast function or differentiation and also functional imbalances between osteoblasts and osteoclasts. The pathological condition most widely studied—since it represents a major economic challenge—is osteoporosis; osteoporosis is characterized by an excessive brittleness of the skeleton due to a decrease in bone mass and to modification of the bone microarchitecture. The solidity of bone results from an equilibrium between the action of two types of bone cells: osteoblasts which solidify bone and osteoclasts (responsible for bone resorption) which embrittle bones. A dominant activity of osteoclasts leads to osteoporosis which can result either from insufficient bone material at the end of growth, or from excessive bone loss during aging. The prevention of osteoporosis can take place via the reduction of a physiological precursor phenomenon, osteopenia (decrease in bone density) which can, before osteoporosis, lead to bone rarefaction disorders and to embrittlement of the bone tissue.

Other pathological conditions are associated with dysfunctions that induce a loss of bone mass; mention may be made of:

osteogenesis imperfecta: this disease is also known as "brittle bone disease" and groups together diseases characterized by excessive bone brittleness due to a congenital defect in the development of the collagen fibers of the connective tissue which forms the framework of the bone. All types are characterized by an extreme bone brittleness, which is the most typical sign of the disease;

hypercalcemia;

hyperparathyroidism;

osteomalacia; which corresponds to bone decalcification induced by a mineralization defect (lack of calcium and phosphate ions) of the protein framework of the skeleton;

osteonecrosis; which covers ailments defined by the death of the cells of the bone tissue;

Paget's disease of bone (osteitis deformans); osteopathy, localized in one or more bones, characterized by excessive bone remodeling resulting in progressive hypertrophy of bone pieces and in considerable abnormalities of the bone microarchitecture;

rheumatoid arthritis;

inflammatory arthritis;

osteomyelitis;

paradontitis;

bone metastases.

Renewal of the bone tissue may also be necessary in situations where it is sought to accelerate bone repair, such as fractures, plastic surgery or the insertion of implants, in particular dental implants.

Osteoblast differentiation is influenced by many signaling pathways, including, for example, the TGB-β (transforming growth factor β1), Hedgehog (Hh) protein, Wnt, FGF (fibroblast growth factor), IGF1 (insulin-like growth factor 1) or BMP (bone morphogenetic protein) pathways (Centrella et al. 1994; Yamaguchi et al. 2000; van der Horst et al. 2003; Fromigue et al. 2004; Hu et al. 2005).

Although BMPs have been used successfully (Johnson and Urist 2000), they are expensive and the doses required in order to carry out efficient cell differentiation are well above the acceptable physiological thresholds. An alternative would be the use of small molecules which make it possible to modulate BMP activity in vivo (Yu et al. 2008).

TGF-β has also been described as a major participant in regulating the balance of the activity between osteoclasts and osteoblasts. Recently, pharmacological inhibitors of its receptor have shown a stimulatory activity on osteoblasts and an inhibitory activity on osteoclasts (Mohammad et al. 2009).

The role of IGF1 has been well studied, but the use of recombinant human IGF1, despite an influence on bone metabolism, has some disadvantages. It does not specifically target the skeleton and causes side effects which limit its use for bone diseases.

The Hedgehog signaling molecule plays a fundamental role in the morphogenesis of numerous tissues, including bone, and also in cell proliferation, and appears to be involved in tissue maintenance and repair in adults (see the reviews by Ingham and McMahon 2001; Wechsler-Reya and Scott 2001; Marti and Bovolenta 2002; Lum and Beachy 2004; Varjosalo and Taipale 2008).

Stimulation of the Hedgehog pathway makes it possible to induce osteogenesis in various models. Several agonist molecules have been studied:

the Hedgehog proteins and derived polypeptides which stimulate osteoblast differentiation by acting on the Patched protein (Spinella-Jaegle et al. 2001; Guan et al. 2009);

purmorphamine which makes it possible to activate human osteoblasts in culture (Wu et al. 2004; Beloti et al. 2005);

small organic molecules such as SAG (Chen et al. 2002);

the Hh Ag1.2 molecules (Frank-Kamenetsky et al. 2002);

oxysterol derivatives (Corcoran and Scott 2006; Amantea et al. 2008) which induce osteoblast differentiation and bone formation (Aghaloo et al. 2007; Dwyer et al. 2007; Yu et al. 2008).

However, it remains useful to identify novel molecules which make it possible to modulate cell differentiation, in particular molecules which have an osteogenic activity, and which make it possible to ally good activity and a limited cost; such molecules would be of particular interest for treating bone-related pathological conditions.

SUMMARY

The inventors have identified compounds of general formula (I) capable of inducing cell differentiation, in particular osteoblast differentiation; these compounds therefore represent novel agents for stimulating the differentiation of stem cells or of progenitor cells into osteoblasts or other cell types.

The term "stem cell" is intended to mean an undifferentiated embryonic or adult cell which is capable of giving specialized cells by cell differentiation and which can renew itself virtually indefinitely. Adult stem cells will preferentially be used.

Progenitor cells are pluripotent adult cells, i.e. cells of which the differentiation can result in several cell types.

In the present application, it is considered that cells are engaged in osteoblast differentiation—they are then described as "cells with an osteoblast phenotype"—when they produce alkaline phosphatase. Such cells are sufficiently engaged in osteoblast differentiation for continued incubation thereof in nutritive medium and/or implantation thereof to enable at least a part of said cells to advance in the differentiation, as far as terminal differentiation (with the production of a mineralized extracellular matrix). The demonstration of the characteristic properties of these cells (namely, alkaline phosphatase production) can be carried out conventionally, for example using the tests mentioned in the experimental section hereinafter.

Consequently, a subject of the present invention is the compounds of general formula (I) below:

(I)

in which:
X, in the ortho, meta or para position, represents —H, —OH, —$NH_2$, a halogen atom, preferably chlorine or bromine, an alkyl radical consisting of a linear or branched carbon-based chain having from 1 to 10 carbon atoms, an alkoxy radical (of formula —O-alkyl where the alkyl group is as previously defined), a cycloalkyl having from 3 to 8 carbon atoms or an aryl group;

$R^8$, in the ortho, meta or para position, on a carbon other than that which bears the X radical, represents: —(C=O)—NH—$R^1$, —(C=O)—O—$R^1$ or —NH—(C=O)—$R^1$;

W represents —H, —OH, —$NH_2$ or a halogen atom, preferably chlorine or bromine;

$R^1$, $R^2$ and $R^3$, which may be identical or different, and independently of one another, represent:
a hydrogen atom; or
an alkyl group consisting of a linear or branched carbon-based chain having from 1 to 10 carbon atoms, optionally unsaturated with one or more double or triple bonds, and optionally substituted with one or more heteroatoms such as O and S, with one or more halogen atoms or with one or more aryl or heteroaryl groups, preferably a pyridine group; or
a cycloalkyl having from 3 to 8 carbon atoms, optionally substituted with an alkyl radical consisting of a linear or branched carbon-based chain having from 1 to 10 carbon atoms or with an alkoxy radical (of formula —O-alkyl where the alkyl group is as previously defined);

$R^4$, $R^5$, $R^6$ and $R^7$, which may be identical or different, and independently of one another, are chosen from —H, —Cl, —Br, —I, —CN, —$NO_2$, an alkyl radical consisting of a linear or branched carbon-based chain having from 1 to 10 carbon atoms, an alkoxy radical (of formula —O-alkyl where the alkyl group is as previously defined) or a cycloalkyl having from 3 to 8 carbon atoms, for example a cyclopropyl, a cyclopentyl or a cyclohexyl;

it being understood that $R^3$ and $R^4$ can be fused so as to form, with the adjacent nitrogen and carbon atoms of the quinoline ring which bears them, a 5- or 6-membered ring;

for use thereof for inducing the cellular differentiation of stem or progenitor cells and more particularly for use thereof for the treatment of diseases caused by dysregulation of osteoblast function or differentiation and/or by a functional imbalance between osteoblasts and osteoclasts, said use making it possible to induce the cellular differentiation of stem or progenitor cells.

For the purposes of the present invention, the term "alkyl" is intended to mean a linear or branched, saturated hydrocarbon-based aliphatic group having from 1 to 10 carbon atoms, preferably from 3 to 8 carbon atoms.

The term "branched" means that at least one lower alkyl group having from 1 to 6 carbon atoms, such as a methyl or an ethyl, is borne by a linear alkyl chain.

The term "halogen atom" is intended to mean a bromine, chlorine, iodine or fluorine atom; the bromine and chlorine designations being preferred.

The term "aryl group" is intended to mean any functional group or substituent derived from at least one aromatic ring; mention may be made of phenyl, benzylcyclobutene, pentalene, naphthalene, benzylphenyl and anthracene groups.

The term "heteroaryl group" is intended to mean any functional group or substituent derived from at least one aromatic ring as defined above and containing at least one heteroatom chosen from P, S, O and N; among heteroaryl groups, mention may be made of furan, pyridine, pyrrole, thiophene, imidazole, pyrazole, oxazole, isoxazole, thiazole, pyrazine, pyrimidine, pyridazine, benzofuran, isobenzofuran, indole, isoindole, benzothiophene, benzo[c]thiophene, benzimidazole, indazole, benzoxazole, benzisoxazole, benzothiazole, quinoline, isoquinoline, quinoxaline, quinazoline, cinnoline, purine and acridine groups.

Preferably, the compounds of general formula (I) are such that the $R^3$ radical is an alkyl radical having from 3 to 8 carbon atoms, such as the hexyl radical; the $R^2$ radical is a hydrogen atom or an alkyl radical having from 1 to 3 carbon atoms; and the $R^4$, $R^5$, $R^6$ and $R^7$ radicals represent a hydrogen atom or an alkyl radical having from 1 to 3 carbon atoms.

Figure 1:
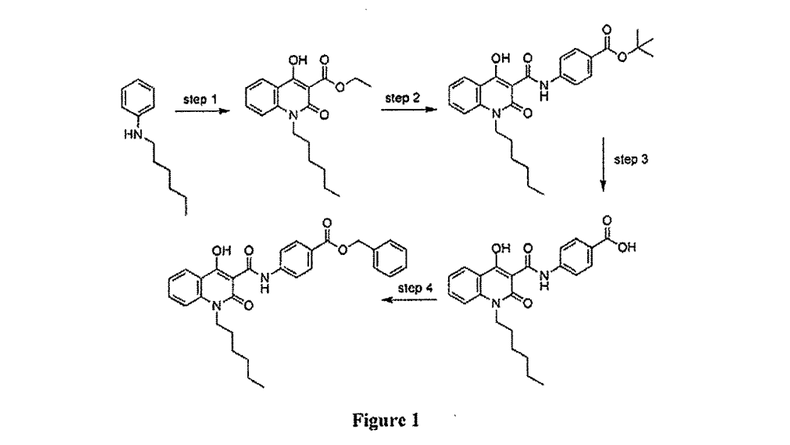
FIG. 1 represents the synthesis scheme for the compounds of general formula (I).
Figure 2:
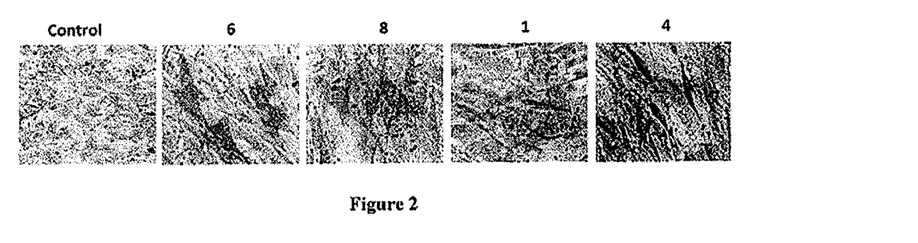
FIG. 2 illustrates the histochemical detection of the alkaline phosphatase induced following differentiation of the mesenchymal stem cells under the action of the compounds of general formula (I). The cells were cultured in the presence of 10 μM of compounds 1, 4, 6 or 8 indicated or of solvent (control) for 6 days in the usual culture medium. The cells were then stained by histochemistry so as to reveal the presence of alkaline phosphatase (red labeling appearing in the form of darker spots), which is a marker for osteogenesis, and then photographed.

By way of compounds of general formula (I), mention may in particular be made, in a nonlimiting manner, of:

propyl 4-(1-hexyl-4-hydroxy-2-oxo-1,2-dihydroquinoline-3-carboxamido)benzoate (compound 1):

ethyl 4-(1-benzyl-4-hydroxy-2-oxo-1,2-dihydroquinoline-3-carboxamido)benzoate (compound 2):

ethyl 4-(1-hexyl-4-hydroxy-2-oxo-1,2-dihydroquinoline-3-carboxamido)benzoate (compound 3):

4-(1-hexyl-4-hydroxy-2-oxo-1,2-dihydroquinoline-3-carboxamido)benzoic acid (compound 4):

butyl 4-(1-hexyl-4-hydroxy-2-oxo-1,2-dihydroquinoline-3-carboxamido)benzoate (compound 5):

tert-butyl 4-(1-hexyl-4-hydroxy-2-oxo-1,2-dihydroquinoline-3-carboxamido)benzoate (compound 6):

benzyl 4-(1-hexyl-4-hydroxy-2-oxo-1,2-dihydroquinoline-3-carboxamido)benzoate (compound 7):

N-(4-(butylcarbamoyl)phenyl)-1-hexyl-4-hydroxy-2-oxo-1,2-dihydroquinoline-3-carboxamide (compound 8):

isopropyl 4-(1-hexyl-4-hydroxy-2-oxo-1,2-dihydroquinoline-3-carboxamido)benzoate (compound 9):

The compounds of general formula (I) in accordance with the invention can be prepared according to the synthesis scheme represented in FIG. 1.

In accordance with the synthesis scheme of FIG. 1, in a first step, an aniline is condensed with triethyl methanetricarboxylate under microwave irradiation so as to obtain quinolinone carboxylates; next, the quinolones are condensed with 4-tert-butylaniline under microwave irradiation so as to give carboxamido-quinolinone esters; the next step consists in saponifying the ester function of these compounds so as to give an acid which is a starting point for various modifications as illustrated in the experimental examples.

The compounds of general formula (I) according to the invention have the property of inducing the differentiation of mesenchymal cells into osteoblasts.

In this respect, these compounds are of interest for the preparation of implants obtained from autologous cells, the differentiation of which into osteoblasts has been induced; these implants are of use for remedying bone tissue losses subsequent to injuries and/or to surgical operations.

The compounds of general formula (I) are therefore of particular interest for the treatment of diseases caused by dysregulation of osteoblast function or differentiation and/or by a functional imbalance between osteoblasts and osteoclasts.

More particularly, these compounds are of use for the treatment of osteoporosis; and of disorders such as brittleness of the skeleton and/or bone rarefaction and/or embrittlement of bone tissue resulting from osteopenia; osteogenesis imperfecta; hypercalcemia; hyperparathyroidism; osteomalacia; osteonecrosis; Paget's disease of bone (osteitis deformans); rheumatoid arthritis; inflammatory arthritis; osteomyelitis; parodontitis; bone metastases.

In addition, the molecules which act more generally on progenitor cell differentiation are of use in the medical or surgical treatment (plastic or reconstructive surgery, tissue or organ transplant) of numerous acute, subacute or chronic, genetic or acquired pathological conditions—involving a tissue dysfunction—for inducing the formation, regeneration, repair and/or increase in activity of tissues such as, in a nonlimiting manner: nervous tissue [central nervous system (brain) and peripheral nervous system (sensory, motor, sympathetic neurons)], bone, cartilage, testicles, liver, spleen, intestine, pancreas, kidneys, smooth and skeletal muscles, heart, lungs, skin and body hair system, mucous membranes, blood cells and immune system cells. By way of nonlimiting example of these pathological conditions, mention may in particular be made of neuropathies and associated neuromuscular diseases, diabetes, alopecia, burns, ulcerations (skin and mucosal) and spermatogenesis disorders.

The present invention also relates to a method for preparing osteoblast cells from stem cells or from progenitor cells, such as mesenchymal cells, comprising the step consisting in incubating, for a sufficient period of time, said cells in a liquid nutritive medium allowing the development of said cells, said nutritive medium containing in solution at least one compound of general formula (I).

In practice, said cells are incubated in the culture medium under standard conditions allowing their development, i.e. not only their survival but also their proliferation and/or their differentiation. The standard conditions for culturing human cells are known: for example, temperature of approximately 37° C.; atmosphere air-$COss$ 95:5; pH close to neutrality.

The culture medium used is a conventional liquid nutritive medium containing the ingredients required for the development of mammalian cells. These ingredients are known. They are mainly mineral salts (in particular, Na, K, Mg, Ca and optionally Cu, Fe, Zn), amino acids, vitamins and carbon sources (for example, glucose). Use may in particular be made of a nutritive medium such as Eagle's minimum essential medium MEM, supplemented with fetal calf serum or, preferably, with autologous human serum.

Use may also be made of more elaborate nutritive media, of the DME (Dulbecco's modified Eagle's medium) type, optionally as a mixture with Ham's F12 medium, with or without serum, and preferably in the presence of autologous serum.

These culture media can be supplemented with osteoinductive factors, such as BMP factors, but, as indicated above, these factors are not necessary for inducing osteoblast differentiation of the human cells used in the method of the invention. Media free of osteoinductive factors can therefore be used.

Preferably, the culture media used are supplemented with osteopromotive factors such as ascorbic acid and beta-glycerophosphates (for example sodium or calcium beta-glycerophosphates).

The present invention also relates to the novel compounds of general formula (Ia):

(Ia)

in which:

- X, in the ortho, meta or para position, represents —H, —OH, —NH$_2$, a halogen atom, preferably chlorine or bromine, an alkyl radical consisting of a linear or branched carbon-based chain having from 1 to 10 carbon atoms, an alkoxy radical (of formula —O-alkyl where the alkyl group is as previously defined), a cycloalkyl having from 3 to 8 carbon atoms or an aryl group;
- $R^8$, in the ortho, meta or para position, on a carbon other than that which bears the X radical, represents: —(C=O)—NH—$R^1$, —(C=O)—O—$R^1$ or —NH—(C=O)—$R^1$;
- W represents —H, —OH, —NH$_2$ or a halogen atom, preferably chlorine or bromine;
- $R^1$ and $R^3$, which may be identical or different, and independently of one another, represent an alkyl group consisting of a linear or branched carbon-based chain having from 3 to 10 carbon atoms, optionally unsaturated with one or more double or triple bonds, and optionally substituted with one or more heteroatoms such as O and S, with one or more halogen atoms or with one or more aryl or heteroaryl groups, preferably a pyridine group;
- $R^4$, $R^5$, $R^6$ and $R^7$, which may be identical or different, and independently of one another, are chosen from —H, —Cl, —Br, —I, —CN, —NO$_2$, an alkyl radical consisting of a linear or branched carbon-based chain having from 1 to 10 carbon atoms, an alkoxy radical (of formula —O-alkyl where the alkyl group is as previously defined) or a cycloalkyl having from 3 to 8 carbon atoms, for example a cyclopropyl, a cyclopentyl or a cyclohexyl;

it being understood that $R^3$ and $R^4$ can be fused so as to form, with the adjacent nitrogen and carbon atoms of the quinoline ring which bears them, a 6-membered ring; with the exclusion of butyl 4-(1-propyl-4-hydroxy-2-oxo-1,2-dihydroquinoline-3-carboxamido)benzoate, as such and for use thereof as medicaments.

The preferred $R^5$ and $R^7$ radicals are chosen, independently of one another, from —H, —Cl, —Br, —CN, and an alkyl radical or an alkoxy radical.

The useful dosage will vary according to the ailment to be treated, the route of administration and the rate of administration, and also the nature and weight of the subject to be treated (human or animal).

The present invention also relates to pharmaceutical compositions characterized in that they comprise, as active ingredient, at least one compound of general formula (Ia) according to the invention, and at least one pharmaceutically acceptable excipient.

In the pharmaceutical compositions in accordance with the invention, the compound(s) of general formula (Ia) is (are) preferably used in an amount which makes it possible to administer unit doses of approximately between 1 mg and 2 g.

Those skilled in the art will select one or more pharmaceutically acceptable excipients according to the route of administration of the pharmaceutical composition. Of course, those skilled in the art will make sure, on this occasion, that the excipient(s) used is (are) compatible with the intrinsic properties associated with the composition in accordance with the present invention.

In addition, the form of the medicament or of the pharmaceutical composition (for example, a solution, a suspension, an emulsion, tablets, capsules, suppositories, etc.) will depend on the route of administration chosen.

Thus, for the purposes of the present invention, the medicament or the pharmaceutical composition can be administered via any suitable route, for example orally, anally, locally, systemically, intravenously, intramuscularly or mucosally, or else using a patch, alternatively in encapsulated form in, or immobilized on, liposomes, microparticles, microcapsules, and the like.

By way of nonlimiting examples of excipients suitable for oral administration, mention may in particular be made of talc, lactose, starch and its derivatives, cellulose and its derivatives, polyethylene glycols, acrylic acid polymers, gelatin, magnesium stearate, animal, vegetable or synthetic fats, paraffin derivatives, glycols, stabilizers, preservatives, antioxidants, wetting agents, anti-caking agents, dispersing agents, emulsifiers, taste modifiers, penetrating agents, solubilizing agents, etc.

The techniques for formulating and administering the medicaments and pharmaceutical compositions are well known in the art under consideration here, it being possible in particular for those skilled in the art to refer to the handbook Remington's Pharmaceutical Sciences (21st edition).

BRIEF DESCRIPTION OF THE DRAWINGS

In addition to the above arrangements, the invention also comprises other arrangements which would emerge from the following description, which refers to examples of synthesis of the compounds of general formula (I), to an example of use of the compounds of general formula (I) according to the present invention, and also to the appended drawings in which.

The curves obtained for compounds 2 to 9 are shown in FIGS. 4 to 11. All these compounds enable the stimulation of differentiation with characteristic differences for each compound. The maximum activity is observed at 10 µM for most of them.

The effect of the following compounds was also tested under the same experimental conditions as those used for compound 1.

DETAILED DESCRIPTION

EXAMPLE 1

Syntheses of Various Compounds of Formula (I)

Preparation of ethyl 1-hexyl-4-hydroxy-2-oxo-1,2-dihydroquinoline-3-carboxylate In a round-bottomed flask equipped with a condenser, N-hexylaniline (355 mg, 2 mmol) is added to a solution of methanetricarboxylic acid triethyl ester (1.35 ml, 6.4 mmol). The resulting reaction mixture is placed in a CEM Discovery microwave oven and irradiated in the open round-bottomed flask, and then the ethanol formed is distilled off (the parameters are the following: power=250 W, temperature=225° C., execution time=5 min, hold time=15 min).

After microwave heating, the reaction crude is purified on a chromatographic column, with petroleum ether, ethyl acetate at 4:1. The crystalline product obtained is dried to give the compound: yield=430 mg (69%). 1H NMR (CDCl$_3$): δ 8.16 (d, J=8 Hz, 1H), 7.64 (m, 1H), 7.27-7.19 (m, 2H), 4.48 (q, J=8 Hz, 2H), 4.18 (t, J=8 Hz, 2H), 1.72-0.86 (m, 14H).

I.A. tert-Butyl 4-(1-hexyl-4-hydroxy-2-oxo-1,2-dihydroquinoline-3-carboxamido)benzoate (compound 6)

Ethyl 1-hexyl-4-hydroxy-2-oxo-1,2-dihydroquinoline-3-carboxylate (159 mg, 0.5 mmol) and tert-butyl 4-aminobenzoate (193 mg, 1 mmol) are suspended in anhydrous toluene (4 ml) and are microwave-heated with the container open (the parameters are the following: power=200 W, temperature=120° C., execution time=7 min, hold time=10 min).

At the end of the reaction, two thirds of the solvent is evaporated off without a condenser. The reaction crude is purified by means of a chromatographic column, using 4:1 petroleum ether:ethyl acetate. The crystalline product obtained is dried to give the title compound: yield=195 mg (84%). 1H NMR (DMSO): δ 8.16 (d, J=8 Hz, 1H), 7.90-7.75 (m, 6H), 7.38 (m, 1H), 4.25 (bs, 2H), 1.60 (bs, 2H), 1.52 (s, 9H), 1.39 (bs, 2H), 1.28 (bs, 5H), 0.84 (bs, 2H).

I.B. 4-(1-hexyl-4-hydroxy-2-oxo-1,2-dihydroquinoline-3-carboxamido)benzoic acid (compound 4)

tert-Butyl 4-(1-hexyl-4-hydroxy-2-oxo-1,2-dihydroquinoline-3-carboxamido)benzoate (83 mg, 0.18 mmol) is added, in fractions, to a solution of trifluoroacetic acid (TFA) cooled to 0° C.; the mixture is allowed to react for 3 hours. The crude product obtained is washed with ethyl ether until a white crystalline solid is formed. The product is dried to give a yield of 61 mg (83%). 1H NMR (DMSO): δ 8.16 (d, J=8 Hz, 1H), 7.96-7.65 (m, 6H), 7.38 (m, 1H), 4.27 (bs, 2H), 1.59 (bs, 2H), 1.39 (bs, 2H), 1.28 (bs, 5H), 0.84 (bs, 2H).

I.C. Benzyl 4-(1-hexyl-4-hydroxy-2-oxo-1,2-dihydroquinoline-3-carboxamido)benzoate (compound 7)

A solution of 4-(1-hexyl-4-hydroxy-2-oxo-1,2-dihydroquinoline-3-carboxamido)benzoic acid (41 mg, 0.1 mmol) in THF is cooled to 0° C., and benzyl alcohol (21 mg, 20 μl, 0.2 mmol) is added, along with EDCI (19 mg, 0.1 mmol) and dimethylaminopyridine (3 mg, 0.02 mmol). The reaction mixture is left to stir overnight. The organic phase is washed with water and evaporated under reduced pressure. The crude product is purified by column chromatography, using 4:1 petroleum ether:ethyl acetate, with a yield of 30 mg (60%). 1H NMR (DMSO): δ 8.16 (d, J=8 Hz, 1H), 8.04 (d, J=8 Hz, 2H), 7.83 (d, J=8 Hz, 3H), 7.68 (d, J=8 Hz, 1H), 7.46-7.25 (m, 6H), 7.38 (m, 1H), 5.30 (s, 2H), 4.28 (bs, 2H), 1.59 (bs, 2H), 1.41-1.15 (m, 6H), 0.84 (bs, 3H).

Example II

Demonstration of the Effect of the Compounds of General Formula (I) on Osteogenesis The effect of the compounds of general formula (I) in accordance with the invention on the stimulation of osteogenesis was determined in vitro by analyzing the differentiation of the C3H10T1/2 pluripotent mesenchymal cell line.

II.1) Materials and Methods

Dissolution of the Compounds, Cell Culture

The test compounds of formula (I) were dissolved in dimethyl sulfoxide (DMSO) to a concentration of 2.5 mM, and then stored at a temperature of −20° C. until use.

The C3H10T1/2 pluripotent fibroblast cell line (ATCC CCL 226) was cultured under the conditions recommended by the ATCC in DMEM culture medium supplemented with 10% of fetal calf serum at a temperature of 37° C. under an atmosphere at 5% $CO_2$. 24 hours after seeding, the cells were stimulated for 6 days in the presence of the compounds of general formula (I) directly diluted in the culture medium. The activation by these compounds causes differentiation of the cell line to the osteoblast lineage and enables the latter to express alkaline phosphatase. Said alkaline phosphatase is then detected by histochemistry or enzymatic assay.

Detection of Alkaline Phosphatase by Histochemistry

For this experiment, the cells are cultured in 6-well plates containing a glass cover slip treated for 1H with 0.05 mg/ml poly-D-lysine. The C3H10T1/2 cells are seeded at a density of 150 000 cells per well. The compounds were applied at a concentration of 10 μM. the Sigma staining kit (85L-3R) was used according to the protocol described. Briefly, after fixing the cells for 30 seconds with a solution of citrate/acetone (2-3) and then rinsing with double-distilled water, the staining is carried out for 30 min in the presence of a solution of Fast-Violet/Naphthol in the dark. The cover slips are then rinsed thoroughly with double-distilled water and then mounted in aqueous medium before being photographed on a DMRXA2 microscope (Leica Microsystems). The cells expressing alkaline phosphatase are stained red.

Enzymatic Assay of Alkaline Phosphatase in 96-Well Plates

The C3H10T1/2 cells were seeded onto 96-well plates at a density of $5 \times 10^3$ cells per well. The compounds were applied at increasing concentrations ranging from 10 nM to 10 μM. The plates were then incubated for 6 days and the assays were then carried out in quadruplicate according to the methods previously described (Chen et al. 2002; Frank-Kamenetsky et al. 2002).

The cells were washed in cold phosphate buffer (PBS) and then lysed by sonication at 4° C. in 50 μl of solution containing 0.9% of NaCl and 0.2% of Triton X-100. The alkaline phosphatase activity in the resulting lysates was then measured according to the method described by Pepinsky et al. (Pepinsky et al. 1998). After the addition of 100 μl of reaction buffer (200 mM Tris-HCl; pH 10.5; 0.4 M of 2-amino-2-methylpropanol and 8 mM of $MgCl_2$) and of 50 μl of substrate (4 mM of disodium p-nitrophenyl phosphate), the lysates were incubated at 37° C. for 60 min, and then the optical density (OD) was measured at a wavelength of 415 nm. By way of comparison, the activity of the SAG compound, which activates osteogenesis by acting on the Hedgehog pathway, was tested under the same conditions. The GraphPad Prism 4° software was used to plot the curves and to determine the effective concentrations 50 ($EC_{50}$).

II.2) Results

II.2-1. Histochemical Demonstration of the Differentiation of the Mesenchymal Stem Cells to the Osteoblast Lineage by the Compounds of Formula (I)

The stimulation of osteogenesis in the C3H10T1/2 pluripotent cells was assessed by observing the induction of alkaline phosphatase (AP). After 6 days of differentiation in the presence of 10 μM of compounds of formula (I), the expression of AP was detected by histochemical staining. By way of example, an increase in the number of cells labeled is observed in the presence of compounds 1, 4, 6 and 8 with more or less strong intensities (compound 4>compound 1>compound 8>compound 6). No cell treated with the solvent (DMSO) expresses AP at a level detectable by this method.

Figure 3:
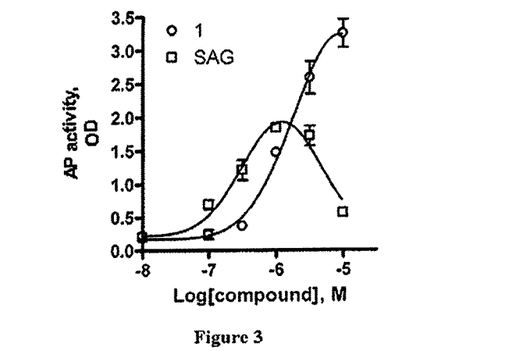
FIG. 3 illustrates the effect of compound 1 on the alkaline phosphatase enzymatic activity which is an indicator of the effect of this compound on the differentiation of C3H10T1/2 mesenchymal stem cells. The differentiation induced by compound 1 is measured via the alkaline phosphatase enzymatic activity (OD at 415 nm) (circles). By way of comparison, the differentiation of the cells obtained in the same experiment with SAG is shown (squares). A representative curve±SD with respect to 5 independent experiments is shown.
Figure 4:
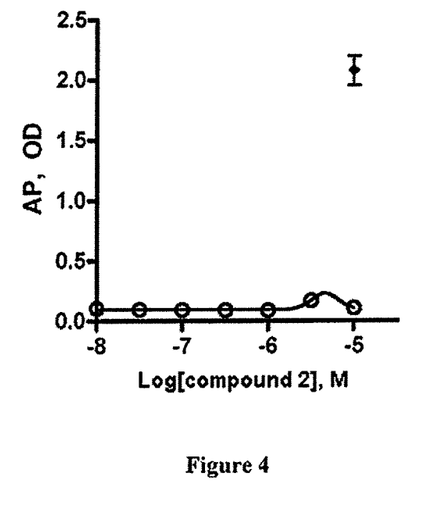
FIG. 4: Differentiation of C3H10T1/2 cells by compound 2. The response to compound 2 was evaluated under the same experimental conditions as those used for compound 1. By way of comparison, the differentiation of the cells obtained in the same experiment with compound 1 (10 µM) is indicated with a diamond. A representative curve with respect to 2-3 independent experiments.
Figure 5:
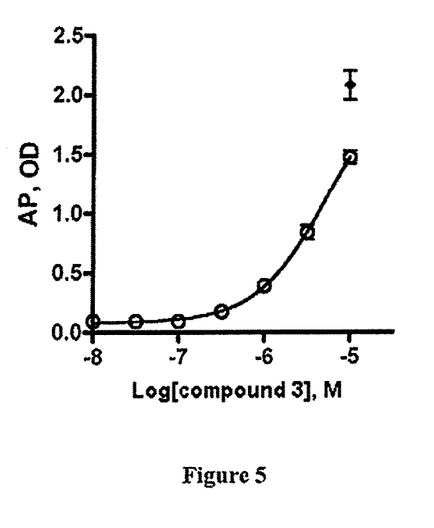
FIG. 5: Differentiation of C3H10T1/2 cells induced by compound 3.
Figure 6:
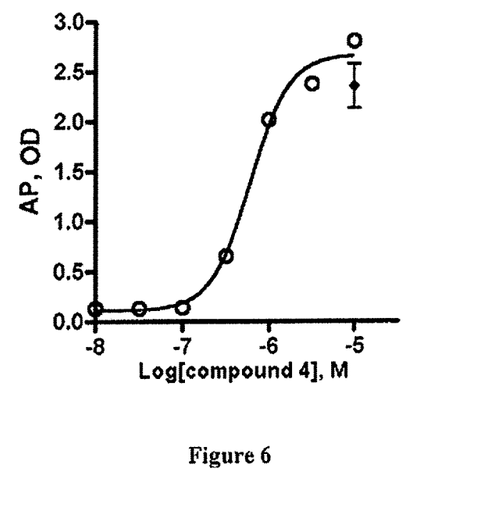
FIG. 6: Differentiation of C3H10T1/2 cells induced by compound 4.
Figure 7:
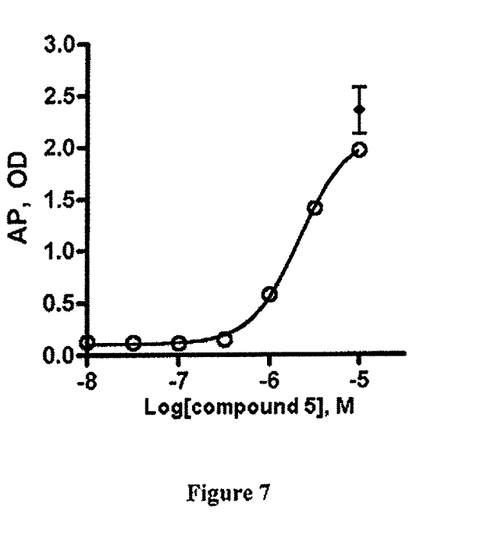
FIG. 7: Differentiation of C3H10T1/2 cells induced by compound 5.
Figure 8:
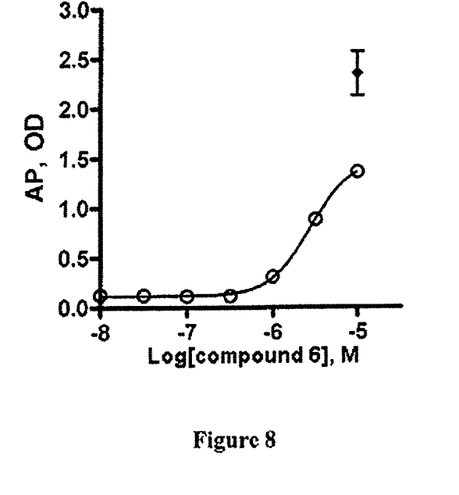
FIG. 8: Differentiation of C3H10T1/2 cells induced by compound 6.
Figure 9:
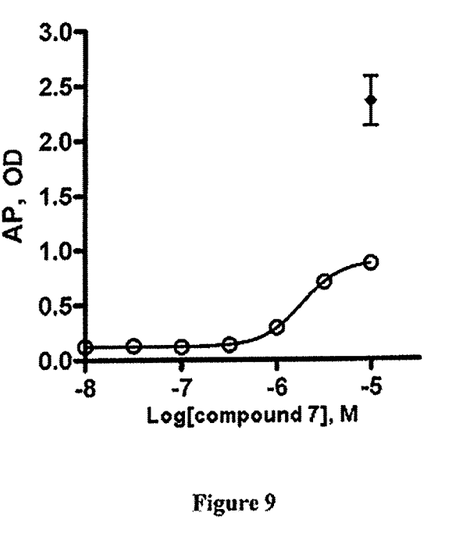
FIG. 9: Differentiation of C3H10T1/2 cells induced by compound 7.
Figure 10:
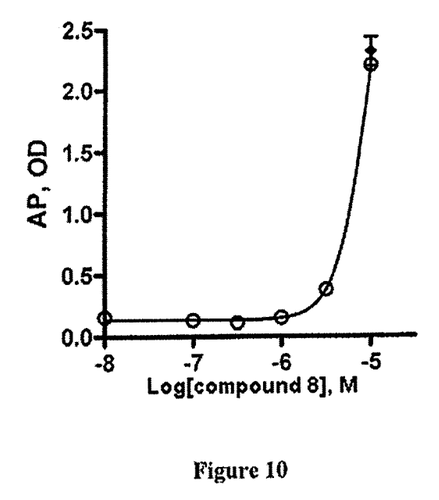
FIG. 10: Differentiation of C3H10T1/2 cells induced by compound 8.
Figure 11:
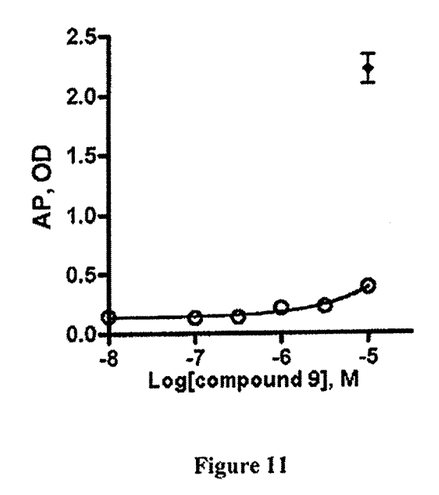
FIG. 11: Differentiation of C3H10T1/2 cells induced by compound 9.

II.2-2. Differentiation of the Mesenchymal Stem Cells by the Compounds of Formula (I): Assaying of the Alkaline Phosphatase Activity The dose-response curves of the compounds of formula (I) were constructed between 10 nM and 10 μM, and the affinities of the compounds with respect to the activation of C3H10T1/2 cell differentiation were determined. FIG. 3 shows a curve representative of compound 1, produced in parallel with that of the smoothened receptor agonist SAG. The latter gives a lower maximum stimulation than compound 1, although their affinities are similar.

The curves obtained for compounds 2 to 9 are shown in FIGS. 4 to 11. All these compounds make it possible to stimulate differentiation with characteristic differences for each compound. The maximum activity is observed at 10 µM for most of them.

The results of the exploitation of these curves are reported in table I hereinafter. The affinities of the compounds are of the order of 1 micromolar. Compound 2 is the least active, with a maximum of 4% of compound 1. Conversely, compound 4 is the one which exhibits the best activity, with an affinity of 0.6 µm and a maximum stimulation which is 20% greater than that of compound 1.

TABLE I

Affinity and maximum activation of the compounds of formula (I) on the differentiation of C3H10T1/2 multipotent cells

| Compound | $EC_{50}$, µM | Activity of the compounds of formula (I) on the differentiation of C3H10T1/2 cells measured via alkaline phosphatase activity Maximum stimulation, % of maximum activation of compound 1 |
|---|---|---|
| 1 | 1.3 | 100 |
| 2 | >3 | 4 |
| 3 | 3.6 | 66 |
| 4 | 0.6 | 124 |
| 5 | 1.5 | 91 |
| 6 | 3.1 | 62 |
| 7 | 2 | 47 |
| 8 | 5.8 | 94 |
| 9 | 6.5 | 33 |

The effective concentration 50 ($EC_{50}$) of the compounds on the differentiation is expressed in µM. The maximum stimulation is expressed as a percentage of that obtained with compound 1 in the same experiment. The data correspond to the mean of 2 to 5 independent experiments.

References

Aghaloo, T. L., C. M. amantea, et al. (2007). "Oxysterols enhance osteoblast differentiation in vitro and bone healing in vivo." *J Orthop Res* 25(11): 1488-97.

Amantea, C. M., W. K. Kim, et al. (2008). "Oxysterol-induced osteogenic differentiation of marrow stromal cells is regulated by Dkk-1 inhibitable and PI3-kinase mediated signaling." *J Cell Biochem* 105(2): 424-36.

Beloti, M. M., L. S. Bellesini, et al. (2005) "Purmorphamine enhances osteogenic activity of human osteoblasts derived from bone marrow mesenchymal cells." *Cell Biol Int* 29(7): 537-41.

Boonen, S., C. Rosen, et al. (2002). "Musculoskeletal effects of the recombinant human IGF-I/IGF binding protein-3 complex in osteoporotic patients with proximal femoral fracture: a double-blind, placebo-controlled pilot study." *J Clin Endocrinol Metab* 87(4): 1593-9.

Centrella, M., M. C. Horowitz, et al. (1994). "Transforming growth factor-beta gene family members and bone." *Endocr Rev* 15(1): 27-39.

Chen, J. K., J. Taipale, et al. (2002). "Small molecule modulation of Smoothened activity." *Proc Natl Acad Sci USA* 99(22): 14071-6.

Corcoran, R. B. and M. P. Scott (2006). "Oxysterols stimulate Sonic hedgehog signal transduction and proliferation of medulloblastoma cells." *Proc Natl Acad Sci USA* 103(22): 8408-13.

Dwyer, J. R., N. Sever, et al. (2007). "Oxysterols are novel activators of the hedgehog signaling pathway in pluripotent mesenchymal cells." *J Biol Chem* 282(12): 8959-68.

Frank-Kamenetsky, M., X. M. Zhang, et al. (2002). "Small-molecule modulators of Hedgehog signaling: identification and characterization of Smoothened agonists and antagonists." *J Biol* 1(2): 10.

Fromigue, O., D. Modrowski, et al. (2004). "Growth factors and bone formation in osteoporosis: roles for fibroblast growth factor and transforming growth factor beta." *Curr Pharm Des* 10(21): 2593-603.

Giustina, A., G. Mazziotti, et al. (2008). "Growth hormone, insulin-like growth factors, and the skeleton." *Endocr Rev* 29(5): 535-59.

Guan, C. C., M. Yan, et al. (2009). "Sonic hedgehog alleviates the inhibitory effects of high glucose on the osteoblastic differentiation of bone marrow stromal cells." *Bone* 45(6): 1146-52.

Hu, H., M. J. Hilton, et al. (2005). "Sequential roles of Hedgehog and Wnt signaling in osteoblast development." *Development* 132(1): 49-60.

Ingham, P. W. and A. P. McMahon (2001). "Hedgehog signaling in animal development: paradigms and principles." *Genes Dev* 15(23): 3059-87.

Johnson, E. E. and M. R. Urist (2000). "Human bone morphogenetic protein allografting for reconstruction of femoral nonunion." *Clin Orthop Relat Res* (371): 61-74.

Lum, L. and P. A. Beachy (2004). "The Hedgehog response network: sensors, switches, and routers." *Science* 304(5678): 1755-9.

Marti, E. and P. Bovolenta (2002). "Sonic hedgehog in CNS development: one signal, multiple outputs." *Trends Neurosci* 25(2): 89-96.

Mohammad, K. S., C. G. Chen, et al. (2009). "Pharmacologic inhibition of the TGF-beta type I receptor kinase has anabolic and anti-catabolic effects on bone". *PLoS One* 4(4): e5275.

Pepinsky, R. B., C. Zeng, et al. (1998). "Identification of a palmitic acid-modified form of human Sonic hedgehog." *J Biol Chem* 273(22): 14037-45.

Spinella-Jaegle, S., G. Rawadi, et al. (2001). "Sonic hedgehog increases the commitment of pluripotent mesenchymal cells into the osteoblastic lineage and abolishes adipocytic differentiation." *J Cell Sci* 114(Pt 11): 2085-94.

van der Horst, G., H. Farih-Sips, et al. (2003). "Hedgehog stimulates only osteoblastic differentiation of undifferentiated KS483 cells."*Bone* 33(6): 899-910.

Varjosalo, M. and J. Taipale (2008). "Hedgehog: functions and mechanisms." *Genes Dev* 22(18): 2454-72.

Wechsler-Reya, R. and M. P. Scott (2001). "The developmental biology of brain tumors." *Annu Rev Neurosci* 24: 385-428.

Wu, X., J. Walker, et al. (2004). "Purmorphamine induces osteogenesis by activation of the hedgehog signaling pathway." *Chem Biol* 11(9): 1229-38.

Yamaguchi, A., T. Komori, et al. (2000). "Regulation of osteoblast differentiation mediated by bone morphogenetic proteins, hedgehogs, and Cbfa1." *Endocr Rev* 21(4): 393-411.

Yu, P. B., C. C. Hong, et al. (2008). "Dorsomorphin inhibits BMP signals required for embryogenesis and iron metabolism." *Nat Chem Biol* 4(1): 33-41.

The invention claimed is:

1. A method for the treatment of diseases caused by one or more of the dysregulation of osteoblast function or differentiation, or by a functional imbalance between osteoblasts and osteoclasts, the method causing inducement of cellular differentiation of stem or progenitor cells, said method comprising the step of administering a compounds of general formula (I):

(I)

(I)

in which:

X, in the ortho, meta or para position, represents —H, —OH, —NH$_2$, a halogen atom, an alkyl radical consisting of a linear or branched carbon-based chain having from 1 to 10 carbon atoms, an alkoxy radical, a cycloalkyl having from 3 to 8 carbon atoms or an aryl group;

R$^8$, in the ortho, meta or para position, on a carbon other than that which bears the X radical, represents: —(C=O)—NH—R$^1$, —(C=O)—O—R$^1$ or —NH—(C=O)—R$^1$;

W represents —H, —OH, —NH$_2$ or a halogen atom;

R$^1$, R$^2$ and R$^3$, which may be identical or different, and independently of one another, represent:

a hydrogen atom; or an alkyl group consisting of a linear or branched carbon-based chain having from 1 to 10 carbon atoms, optionally unsaturated with one or more double or triple bonds, and optionally substituted with one or more heteroatoms, with one or more halogen atoms or with one or more aryl or heteroaryl groups; or a cycloalkyl having from 3 to 8 carbon atoms, optionally substituted with an alkyl radical consisting of a linear or branched carbon-based chain having from 1 to 10 carbon atoms or with an alkoxy radical;

R$^4$, R$^5$, R$^6$ and R$^7$, which may be identical or different, and independently of one another, are chosen from —H, —Cl, —Br, —I, —CN, —NO$_2$, an alkyl radical consisting of a linear or branched carbon-based chain having from 1 to 10 carbon atoms, an alkoxy radical or a cycloalkyl having from 3 to 8 carbon atoms;

it being understood that R$^3$ and R$^4$ can be fused so as to form, with the adjacent nitrogen and carbon atoms of the quinoline ring which bears them, a 5- or 6-membered ring, and wherein the disease is selected from the group consisting of osteoporosis, brittleness of the skeleton, bone rarefaction, embrittlement of bone tissue resulting from osteopenia, osteogenesis imperfect, hypercalcemia, bone resorption associated with hyperparathyroidism, osteomalacia, osteonecrosis, bone resorption associated with Paget's disease of bone (osteitis deformans), rheumatoid arthritis, inflammatory arthritis, osteomyelitis, paradontitis, and bone resorption associated with bone metastases, and combinations thereof.

2. A method for preparing implants of autologous cells differentiated into osteoblasts for remedying bone tissue losses subsequent to injuries and/or to surgical operations, comprising a step of inducing the differentiation of mesenchymal cells into osteoblasts by a compound of general formula (I):

in which:

X, in the ortho, meta or para position, represents —H, —OH, —NH$_2$, a halogen atom, an alkyl radical consisting of a linear or branched carbon-based chain having from 1 to 10 carbon atoms, an alkoxy radical, a cycloalkyl having from 3 to 8 carbon atoms or an aryl group;

R$^8$, in the ortho, meta or para position, on a carbon other than that which bears the X radical, represents: —(C=O)—NH—R$^1$, —(C=O)—O-R$^1$ or —NH—(C=O)—R$^1$;

W represents —H, —OH, —NH$_2$ or a halogen atom;

R$^1$, R$^2$ and R$^3$, which may be identical or different, and independently of one another, represent:

a hydrogen atom; or an alkyl group consisting of a linear or branched carbon-based chain having from 1 to 10 carbon atoms, optionally unsaturated with one or more double or triple bonds, and optionally substituted with one or more heteroatoms, with one or more halogen atoms or with one or more aryl or heteroaryl groups; or a cycloalkyl having from 3 to 8 carbon atoms, optionally substituted with an alkyl radical consisting of a linear or branched carbon-based chain having from 1 to 10 carbon atoms or with an alkoxy radical;

R$^4$, R$^5$, R$^6$ and R$^7$, which may be identical or different, and independently of one another, are chosen from —H, —Cl, —Br, —I, —CN, —NO$_2$, an alkyl radical consisting of a linear or branched carbon-based chain having from 1 to 10 carbon atoms, an alkoxy radical or a cycloalkyl having from 3 to 8 carbon atoms;

it being understood that R$^3$ and R$^4$ can be fused so as to form, with the adjacent nitrogen and carbon atoms of the quinoline ring which bears them, a 5- or 6-membered ring.

3. The method according to claim 1, wherein said R$^3$ radical is an alkyl radical having from 3 to 8 carbon atoms; the R$^2$ radical is a hydrogen atom or an alkyl radical having from 1 to 3 carbon atoms; and the R$^4$, R$^5$, R$^6$ and R$^7$ radicals represent a hydrogen atom or an alkyl radical having from 1 to 3 carbon atoms.

4. The method according claim 1, wherein the compound is chosen from:

propyl 4-(1-hexyl-4-hydroxy-2-oxo-1,2-dihydroquinoline-3-carboxamido)benzoate (compound 1);

ethyl 4-(1-benzyl-4-hydroxy-2-oxo-1,2-dihydroquinoline-3carboxamido)benzoate (compound 2);

ethyl 4-(1-hexyl-4-hydroxy-2-oxo-1,2-dihydroquinoline-3-carboxamido)benzoate (compound 3);

4-(1-hexyl-4-hydroxy-2-oxo-1,2-dihydroquinoline-3-carboxamido)benzoic acid (compound 4);

butyl 4-(1-hexyl-4-hydroxy-2-oxo-1,2-dihydroquinoline-3-carboxamido)benzoate (compound 5);

tert-butyl 4-(1-hexyl-4-hydroxy-2-oxo-1,2-dihydroquinoline-3-carboxamido)benzoate (compound 6);

benzyl 4-(1-hexyl-4-hydroxy-2-oxo-1,2-dihydroquinoline-3-carboxamido)benzoate (compound 7);

N-(4-(butylcarbamoyl)phenyl)-1-hexyl-4-hydroxy-2-oxo-1,2-dihydroquinoline-3-carboxamide (compound 8); or isopropyl 4-(1-hexyl-4-hydroxy-2-oxo-1,2-dihydroquinoline-3-carboxamido)benzoate (compound 9).

5. Compounds of general formula (Ia):

in which:

X, in the ortho, meta or para position, represents —H, —OH, —NH$_2$, a halogen atom, an alkyl radical consisting of a linear or branched carbon-based chain having from 1 to 10 carbon atoms, an alkoxy radical, a cycloalkyl having from 3 to 8 carbon atoms or an aryl group;

R$^8$, in the ortho, meta or para position, on a carbon other than that which bears the X radical, represents: —(C=O)—NH—R$^1$, —(C=O)—O—R$^1$ or —NH—(C=O)—R$^1$;

W represents —H, —OH, —NH$_2$ or a halogen atom;

R$^1$ and R$^3$, which may be identical or different, and independently of one another, represent an alkyl group consisting of a linear or branched carbon-based chain having from 3 to 10 carbon atoms, optionally unsaturated with one or more double or triple bonds, and optionally substituted with one or more heteroatoms, with one or more halogen atoms or with one or more aryl or heteroaryl groups;

R$^4$, R$^5$, R$^6$ and R$^7$, which may be identical or different, and independently of one another, are chosen from —H, —Cl, —Br, —I, —CN, —NO$_2$, an alkyl radical consisting of a linear or branched carbon-based chain having from 1 to 10 carbon atoms, an alkoxy radical or a cycloalkyl having from 3 to 8 carbon atoms;

it being understood that R$^3$ and R$^4$ can be fused so as to form, with the adjacent nitrogen and carbon atoms of the quinoline ring which bears them, a 6-membered ring;

with the exclusion of butyl 4-(1-propyl-4-hydroxy-2-oxo-1,2-dihydroquinoline-3-carboxamido)benzoate.

6. The compounds of general formula (Ia) as claimed in claim 5, as a medicament.

7. A pharmaceutical composition comprising as an active ingredient, at least one compound of general formula (Ia) as claimed in claim 5, and at least one pharmaceutically acceptable excipient.

8. A method for the treatment of diseases caused by dysregulation of osteoblast function or differentiation and/or by a functional imbalance between osteoblasts and osteoclasts, said method making it possible to induce the cellular differentiation of stem or progenitor cells, the method comprising the step of administering a compound of general formula (Ia) according to claim 5, and wherein the disease is selected from the group consisting of osteoporosis, brittleness of the skeleton, bone rarefaction, embrittlement of bone tissue resulting from osteopenia, osteogenesis imperfect, hypercalcemia, bone resorption associated with hyperparathyroidism, osteomalacia, osteonecrosis, bone resorption associated with Paget's disease of bone (osteitis deformans), rheumatoid arthritis, inflammatory arthritis, osteomyelitis, paradontitis, and bone resorption associated with bone metastases, and combinations thereof.

9. A method for preparing implants of autologous cells differentiated into osteoblasts for remedying bone tissue losses subsequent to injuries and/or to surgical operations, comprising a step of inducing the differentiation of mesenchymal cells into osteoblasts by a compound of general formula (Ia) according to claim 5.

* * * * *

UNITED STATES PATENT AND TRADEMARK OFFICE
CERTIFICATE OF CORRECTION

PATENT NO.       : 9,061,997 B2                                Page 1 of 1
APPLICATION NO.  : 13/885089
DATED            : June 23, 2015
INVENTOR(S)      : Ruat et al.

It is certified that error appears in the above-identified patent and that said Letters Patent is hereby corrected as shown below:

On the Title page,
Item (75) Inventors: "Castelnuevo" should read --Castelnuovo--.

Signed and Sealed this
Twenty-ninth Day of December, 2015

Michelle K. Lee
*Director of the United States Patent and Trademark Office*